(12) United States Patent
Iwawaki

(10) Patent No.: US 8,482,742 B2
(45) Date of Patent: Jul. 9, 2013

(54) MEASURING APPARATUS AND MEASURING METHOD

(75) Inventor: Takanori Iwawaki, Hachioji (JP)

(73) Assignee: Seiko Epson Corporation, Tokyo (JP)

( * ) Notice: Subject to any disclaimer, the term of this patent is extended or adjusted under 35 U.S.C. 154(b) by 569 days.

(21) Appl. No.: 12/696,686

(22) Filed: Jan. 29, 2010

(65) Prior Publication Data

US 2010/0201987 A1    Aug. 12, 2010

(30) Foreign Application Priority Data

Feb. 6, 2009  (JP) ................. 2009-026332
Feb. 6, 2009  (JP) ................. 2009-026333
Feb. 6, 2009  (JP) ................. 2009-026334

(51) Int. Cl.
*G01B 11/30* (2006.01)
(52) U.S. Cl.
USPC ........... 356/601; 356/39; 356/445; 356/343; 600/310; 600/475; 600/477
(58) Field of Classification Search
USPC ..... 356/39–42, 432–436, 445–448, 337–343, 356/416; 600/309, 310, 322–323, 364, 407, 600/473, 475, 476, 477
See application file for complete search history.

(56) References Cited

U.S. PATENT DOCUMENTS

| 4,714,080 A | 12/1987 | Edgar, Jr. et al. | |
| 4,877,322 A * | 10/1989 | Hill | 600/318 |
| 5,487,472 A | 1/1996 | Satake et al. | |
| 6,819,950 B2 * | 11/2004 | Mills | 600/322 |
| 7,470,235 B2 | 12/2008 | Moriya et al. | |

FOREIGN PATENT DOCUMENTS

| JP | A-63-92335 | 4/1988 |
| JP | A-07-096253 | 4/1995 |
| JP | A-10-323630 | 12/1998 |
| JP | A-2002-065645 | 3/2002 |
| JP | A-2004-219379 | 8/2004 |
| JP | A-2005-024825 | 1/2005 |
| JP | A-2006-271896 | 10/2006 |

* cited by examiner

*Primary Examiner* — Gregory J Toatley
*Assistant Examiner* — Iyabo S Alli
(74) *Attorney, Agent, or Firm* — Oliff & Berridge, PLC

(57) ABSTRACT

A measuring apparatus includes a filter that transmits light of a predetermined wavelength; a first light receiving unit receives at least one of a first light that is output from a first light source, reflected by or transmitted through an object to be measured, and transmitted through the filter and a second light that is output from a second light source, reflected by or transmitted through the object to be measured, and transmitted through the filter, and through which a signal according to the received light travels; a second light receiving unit receives light of a different path from that received by the first light receiving unit; a difference extracting unit that obtains a difference signal between the signals traveling through the first and second light receiving units and an information generating unit that generates information of the object to be measured based on the difference signal.

18 Claims, 12 Drawing Sheets

MEASURING APPARATUS AND MEASURING METHOD

BACKGROUND

1. Technical Field

The present invention relates to a technique of performing measurement using light.

2. Related Art

An apparatus for measuring blood oxygen saturation level by irradiating a living body with light from a light source that outputs light for measurement and detecting the light reflected from blood of the living body through a light receiving element (e.g. JP-A-63-92335) and an apparatus for measuring a pulse wave by detecting light reflected from blood of a living body through a light receiving element (e.g. JP-A-2006-271896) have been proposed.

SUMMARY

According to an embodiment of the invention, there is provided a measuring apparatus which includes a filter that transmits light of a predetermined wavelength; a first light receiving unit which receives at least one of a first light that is output from a first light source, reflected by or transmitted through an object to be measured, and transmitted through the filter and a second light that is output from a second light source, reflected by or transmitted through the object to be measured, and transmitted through the filter, and through which a signal in response to the received light travels; a second light receiving unit which receives light of a different path from the light received by the first light receiving unit, and through which a signal in response to the received light travels; a difference extracting unit that obtains a difference signal between the signal traveling through the first light receiving unit and the signal traveling through the second light receiving unit; and an information generating unit that generates information of the object to be measured based on the signal obtained from the difference extracting unit.

In a preferred embodiment of the invention, the first light receiving unit receives a first reflected light that is output from the first light source, reflected by the object to be measured, and transmitted through the filter and a second reflected light that is output from the second light source, reflected by the object to be measured, and transmitted through the filter; and the second light receiving unit receives a third reflected light that is output from the second light source, reflected by the object to be measured, and transmitted through the filter.

In another preferred embodiment of the invention, the measuring apparatus includes the first light source; and a second filter that transmits the light having the same wavelength as the light transmitted through the filter among the light output from the first light source; wherein the object to be measured may be irradiated with the light that is output from the first light source and transmitted through the second filter.

In a further preferred embodiment of the invention, the light output from the first light source includes light having a plurality of wavelengths, and the wavelength of the light that is transmitted through the filter and the second filter is changed in response to an input signal.

In a still further preferred embodiment of the invention, the measuring apparatus includes the first light source. The filter has a first filter and a second filter. The first filter transmits the light of an assigned wavelength among the light that is output from the first light source and transmitted through the object to be measured and the light that is output from the second light source and transmitted through the object to be measured. The second filter transmits the light of a determined wavelength among scattered light that is output from the first light source and transmitted through the object to be measured and the light that is output from the second light source and transmitted through the object to be measured. The first light receiving unit receives the light that is transmitted through the first filter. The second light receiving unit receives the light that is transmitted through the second filter. Here, the measuring apparatus includes a control unit that assigns a wavelength to the first filter and controls the first light source. The control unit controls the first light source so that no light is output from the first light source, and stores in a storage unit a first signal that is obtained from the difference extracting unit when the wavelength that is assigned to the first filter by the control unit is longer than the wavelength of the light that is transmitted through the second filter. The control unit controls the first light source so that the light is output from the first light source, and stores in the storage unit a second signal that is obtained from the difference extracting unit when the wavelength that is assigned to the first filter by the control unit is longer than the wavelength of the light that is transmitted through the second filter. The control unit stores in the storage unit, a third signal that indicates the difference between the first signal and the second signal that are stored in the storage unit. The control unit controls the first light source so that the light is output from the first light source, and includes a correcting unit that corrects the signal that is obtained from the difference extracting unit when the wavelength that is assigned to the first filter by the control unit is equal to the wavelength of the light that is transmitted through the second filter with the third signal that is stored in the storage unit. The information generating unit generates information of the object to be measured from the signal corrected by the correcting unit.

In a still further preferred embodiment of the invention, the measuring apparatus includes the first light source. The filter has a first filter and a second filter. The first filter transmits the light of an assigned wavelength among the light that is output from the first light source and reflected by the object to be measured and the light that is output from the second light source and reflected by the object to be measured. The second filter transmits the light of a determined wavelength among scattered light that is output from the first light source and reflected by the object to be measured and the light that is output from the second light source and reflected by the object to be measured. The first light receiving unit receives the light that is transmitted through the first filter; and the second light receiving unit receives the light that is transmitted through the second filter. Here, wherein the measuring apparatus includes a control unit that assigns a wavelength to the first filter and controls the first light source. The control unit controls the first light source so that no light is output from the first light source, and stores in a storage unit a first signal that is obtained from the difference extracting unit when the wavelength that is assigned to the first filter by the control unit is longer than the wavelength of the light that is transmitted through the second filter. The control unit controls the first light source so that the light is output from the first light source, and stores in the storage unit a second signal that is obtained from the difference extracting unit when the wavelength that is assigned to the first filter by the control unit is longer than the wavelength of the light that is transmitted through the second filter. The control unit stores in the storage unit, a third signal that indicates the difference between the first signal and the second signal that are stored in the storage unit. The control unit controls the first light source so that the light is output from the first light source, and includes a correcting unit that corrects the signal that is obtained from the difference extracting unit when the wavelength that is assigned to the first filter by the control unit is equal to the wavelength of the light that is transmitted through the second filter with the third signal that is stored in the storage unit. The information generating unit generates information of the object to be measured from the signal corrected by the correcting unit.

In a still further preferred embodiment of the invention, the measuring apparatus includes a third filter that transmits light of a predetermined wavelength, wherein the wavelength of the light transmitted through the second filter is equal to the wavelength of the light transmitted through the third filter, and the light output from the first light source is transmitted through the third filter and output to the object to be measured.

In a still further preferred embodiment of the invention, the light output from the first light source includes light having a plurality of wavelengths.

In a still further preferred embodiment of the invention, the measuring apparatus includes the first light source. The first light receiving unit receives measuring light that is output from the first light source, transmitted through the object to be measured, and then transmitted through the filter and the light that is output from the second light source, transmitted through the object to be measured, and then transmitted through the filter. The second light receiving unit receives scattered light that is output from the first light source, transmitted through the object to be measured, and then transmitted through the filter and the light that is output from the second light source, transmitted through the object to be measured, and then transmitted through the filter. Here, the measuring apparatus includes a control unit that controls the first light source and the first light receiving unit; the control unit controls the first light source so that no light is output from the first light source, and stores in a storage unit a first signal that is obtained from the difference extracting unit when the first light receiving unit is controlled by the control unit so that the first light receiving unit does not respond to the light. The control unit controls the first light source control unit so that the light is output from the first light source, and stores in the storage unit a second signal that is obtained from the difference extracting unit when the first light receiving unit is controlled by the control unit so that the first light receiving unit does not respond to the light. The control unit stores in the storage unit, a third signal that indicates the difference between the first signal and the second signal that are stored in the storage unit in the storage unit. The control unit controls the first light source so that the light is output from the first light source, and includes a correcting unit that corrects the signal that is obtained from the difference extracting unit when the first light receiving unit is controlled by the control unit so that the first light receiving unit responds to the light with the third signal that is stored in the storage unit. The information generating unit generates information of the object to be measured from the signal corrected by the correcting unit.

In a still further preferred embodiment of the invention, the measuring apparatus includes the first light source. The first light receiving unit receives measuring light that is output from the first light source, reflected by the object to be measured, and then transmitted through the filter and the light that is output from the second light source, reflected by the object to be measured, and then transmitted through the filter. The second light receiving unit receives scattered light that is output from the first light source, reflected by the object to be measured, and then transmitted through the filter and the light that is output from the second light source, reflected by the object to be measured, and then transmitted through the filter. Here, the measuring apparatus includes a control unit that controls the first light source and the first light receiving unit. The control unit controls the first light source so that no light is output from the first light source, and stores in a storage unit a first signal that is obtained from the difference extracting unit when the first light receiving unit is controlled by the control unit so that the first light receiving unit does not respond to the light. The control unit controls the first light source so that the light is output from the first light source, and stores in the storage unit a second signal that is obtained from the difference extracting unit when the first light receiving unit is controlled by the control unit so that the first light receiving unit does not respond to the light. The control unit stores in the storage unit, a third signal that indicates the difference between the first signal and the second signal that are stored in the storage unit. The control unit controls the first light source so that the light is output from the first light source, and includes a correcting unit that corrects the signal that is obtained from the difference extracting unit when the first light receiving unit is controlled by the control unit so that the first light receiving unit responds to the light with the third signal that is stored in the storage unit. The information generating unit generates information of the object to be measured from the signal corrected by the correcting unit.

In a still further preferred embodiment of the invention, the measuring apparatus includes a second filter that transmits the light having the same wavelength as the light transmitted through the filter, wherein the object to be measured may be irradiated with the light that is output from the first light source and transmitted through the second filter.

According to another embodiment of the invention, there is provided a measuring method which includes receiving at least one of a first light that is output from a first light source, reflected by or transmitted through an object to be measured, and transmitted through a filter that transmits light of a predetermined wavelength and a second light that is output from a second light source, reflected by or transmitted through the object to be measured, and transmitted through the filter by a first light receiving unit, and sending a signal in response to the received light through the first light receiving unit; receiving by a second light receiving unit, light of a different path from the light received by the first light receiving unit, and sending a signal in response to the received light through the second light receiving unit; obtaining a difference signal between the signal sent through the first light receiving unit and the signal sent through the second light receiving unit by a difference extracting unit; and generating information of the object to be measured based on the signal obtained from the difference extracting unit by an information generating unit.

In a preferred embodiment of the invention, the measuring method includes stopping an output of light from a first light source that outputs the light to the object to be measured; assigning firstly a predetermined first wavelength to a first filter which the light that is output from the first light source and transmitted through the object to be measured and the light that is output from the second light source and transmitted through the object to be measured can reach and which transmits the light of the assigned wavelength; storing firstly a difference signal between the signal output from the first light receiving unit that outputs the signal according to the light transmitted through the first filter and the signal output from the second light receiving unit that outputs the signal according to the light transmitted through a second filter which scattered light that is output from the first light source and transmitted through the object to be measured and the light that is output from the second light source and transmitted through the object to be measured can reach and which transmits the light of a second wavelength that is output from the first light source; outputting the light from the first light source; storing secondly a difference signal between the signal output from the first light receiving unit and the signal output from the second light receiving unit as a step following the outputting step; storing thirdly a difference signal between the signal stored in the first storing step and the signal stored in the second storing step; assigning secondly the second wavelength to the first filter; and correcting the difference signal between the signal output from the first light receiving unit and the signal output from the second light receiving unit with the signal that is stored in the third storing step as a step following the second assigning step; wherein the information of the object to be measured is generated from the signal corrected in the correction step.

In another preferred embodiment of the invention, the measuring method includes stopping an output of light from a first light source that outputs the light to the object to be measured; assigning firstly a predetermined first wavelength to a first filter which the light that is output from the first light source and reflected by the object to be measured and the light that is output from the second light source and reflected by the object to be measured can reach and which transmits the light of the assigned wavelength; storing firstly a difference signal between the signal output from the first light receiving unit that outputs the signal according to the light transmitted through the first filter and the signal output from the second light receiving unit that outputs the signal according to the light transmitted through a second filter which scattered light that is output from the first light source and reflected by the object to be measured and the light that is output from the second light source and reflected by the object to be measured can reach and which transmits the light of a second wavelength that is output from the first light source; outputting the light from the first light source; storing secondly a difference signal between the signal output from the first light receiving unit and the signal output from the second light receiving unit as a step following the outputting step; storing thirdly a difference signal between the signal stored in the first storing step and the signal stored in the second storing step; assigning secondly the second wavelength to the first filter; and correcting the difference signal between the signal output from the first light receiving unit and the signal output from the second light receiving unit with the signal that is stored in the third storing step as a step following the second assigning step; wherein the information of the object to be measured may be generated from the signal corrected in the correction step.

In a further preferred embodiment of the invention, the measuring method includes stopping an output of light from a first light source that outputs the light to the object to be measured; controlling firstly the first light receiving unit, which can receive measuring light that is output from the first light source, transmitted through the object to be measured, and then transmitted through the filter that transmits the light of the predetermined wavelength and the light that is output from the second light source, transmitted through the object to be measured, and then transmitted through the filter and which outputs a signal according to the received light, so that the first light receiving unit does not respond to the light; storing firstly a difference signal between the signal output from the first light receiving unit and the signal output from the second light receiving unit, which can receive scattered light that is output from the first light source and transmitted through the object to be measured and the light that is output from the second light source and transmitted through the object to be measured and which outputs a signal according to the received light, as a step following the first control step; outputting the light from the first light source; storing secondly a difference signal between the signal from the first light receiving unit and the signal from the second light receiving unit as a step following the outputting step; storing thirdly a difference signal between the signal stored in the first storing step and the signal stored in the second storing step; controlling secondly the first light receiving unit so that the first light receiving unit responds to the light; and correcting the difference signal between the signal from the first light receiving unit and the signal from the second light receiving unit with the signal that is stored in the third storage step as a step following the second control step; wherein the information of the object to be measured is generated from the signal corrected in the correction step.

In a still further preferred embodiment of the invention, the measuring method includes stopping an output of light from a first light source that outputs the light to the object to be measured; controlling firstly the first light receiving unit, which can receive measuring light that is output from the first light source, reflected by the object to be measured, and then transmitted through the filter that transmits the light of the predetermined wavelength and the light that is output from the second light source, reflected by the object to be measured, and then transmitted through the filter and which outputs a signal according to the received light, so that the first light receiving unit does not respond to the light; storing firstly a difference signal between the signal output from the first light receiving unit and the signal output from the second light receiving unit, which can receive scattered light that is output from the first light source and reflected by the object to be measured and the light that is output from the second light source and reflected by the object to be measured and which outputs a signal according to the received light, as a step following the first control step; outputting the light from the first light source; storing secondly a difference signal between the signal from the first light receiving unit and the signal from the second light receiving unit as a step following the outputting step; storing thirdly a difference signal between the signal stored in the first storing step and the signal stored in the second storing step; controlling secondly the first light receiving unit so that the first light receiving unit responds to the light; and correcting the difference signal between the signal from the first light receiving unit and the signal from the second light receiving unit with the signal that is stored in the third storage step as a step following the second control step; wherein the information of the object to be measured is generated from the signal corrected in the correction step.

BRIEF DESCRIPTION OF THE DRAWINGS

The invention will be described with reference to the accompanying drawings, wherein like numbers reference like elements.

DESCRIPTION OF EXEMPLARY EMBODIMENTS

1. First Embodiment

1-1. Whole Configuration

Figure 1:
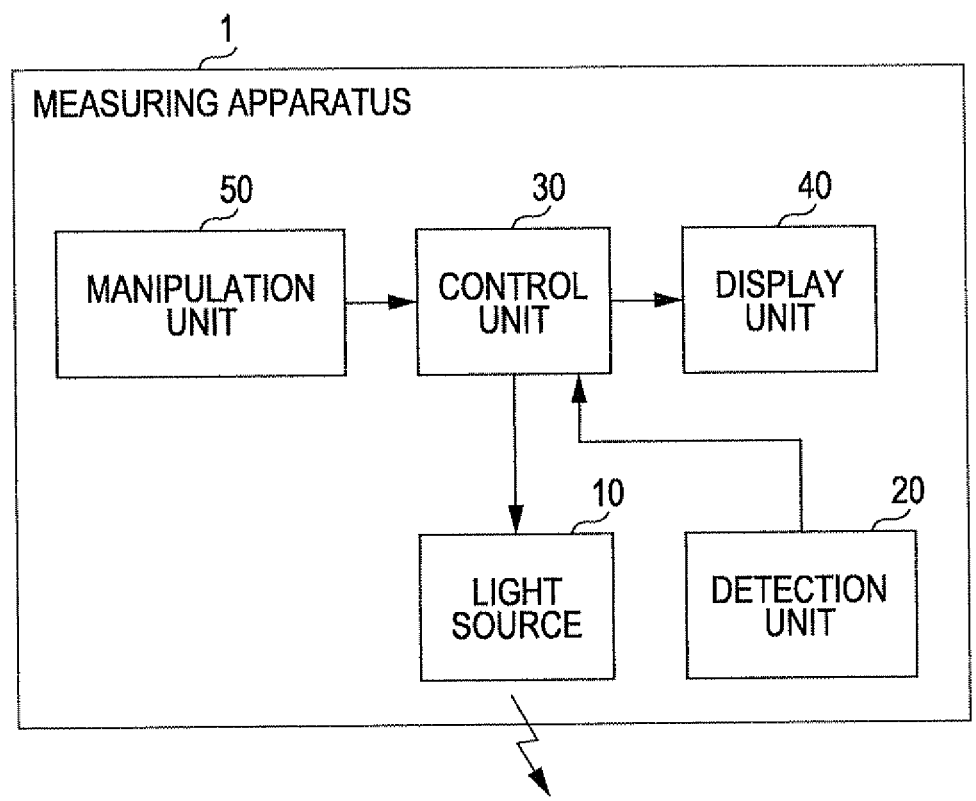
FIG. 1 is a block diagram illustrating the hardware configuration of a measuring apparatus according to a first embodiment of the invention.

FIG. 1 is a block diagram illustrating the hardware configuration of a measuring apparatus 1 according to a first embodiment of the invention. The measuring apparatus 1 is an apparatus for measuring the pulse or pulse wave of a living body. The measuring apparatus 1 includes a light source 10, a detection unit 20, a control unit 30, a display unit 40, and a manipulation unit 50. The light source 10 is provided with a light emitting diode that outputs light. The light source 10 irradiates a living body with light from the light emitting diode onto a living body. The detection unit 20 is provided with a light receiving element that converts light into an electrical signal. The detection unit 20 receives the light reflected from the living body through the light receiving element, and outputs a signal corresponding to the received light. The control unit 30 is so called a microcomputer that is provided with a central processing unit (CPU), a read only memory (ROM), a random access memory (RAM), an input port, and an output port. The control unit 30 operates in accordance with a program stored in the ROM, and controls the light source 10. The control unit 30 measures the pulse or pulse wave of a living body by analyzing the signal output from the detection unit 20. The control unit 30 controls the display unit 40 to display the results of measurement. The display unit 40 is provided with a liquid crystal display. The display unit 40 displays the result of measurement performed by the control unit 30. In this case, as the display unit 40, another display device other than the liquid crystal display, such as a display device using an organic electro-luminescence (EL), may be used. The manipulation unit 50 is connected to the control unit 30, and is provided with manipulation keys for manipulating the measuring apparatus 1. The control unit 30 monitors the manipulation performed by the manipulation key, and performs control of the light source 10 or display of the measurement results in accordance with the performed manipulation.

1-2. Electrical Configuration

Figure 2:
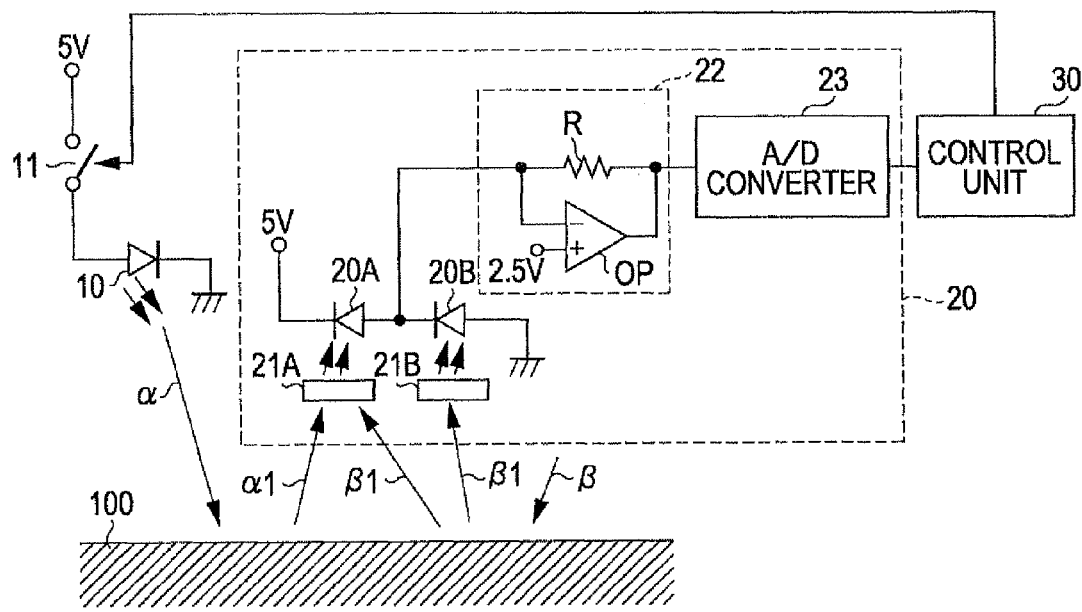
FIG. 2 is a view illustrating the electrical configuration of a light source and a detection unit.

FIG. 2 is a view illustrating the electrical configuration of a light source 10 and a detection unit 20. In this embodiment of the invention, the light source 10 is composed of a light emitting diode that outputs light having a predetermined single wavelength. A switch 11 is connected to the light source 10. The switch 11 is switched to an open/close state in accordance with a signal from the control unit 30.

A first light receiving element 20A (i.e. an example of the first light receiving unit) and a second light receiving element 20B (i.e. an example of the second light receiving unit) are photodiodes through which current flows in response to the received light. The first light receiving element 20A and the second light receiving element 20B are connected in series. An anode of the first light receiving element 20A is connected to a cathode of the second light receiving element 20B. In this embodiment of the invention, the positions of the light source 10, the first light receiving element 20A, and the second light receiving element 20B are set so that the light which is output from the light source 10 and is reflected by a living body 100 does not reach the second light receiving element 20B.

A first filter 21A and a second filter 21B are optical filters (i.e. example of filters) that transmit the light having a predetermined wavelength λ. The first filter 21A is arranged in a light receiving part of the first light receiving element 20A. The second filter 21B is arranged in a light receiving part of the second light receiving element 20B. The light, having passed through the first filter 21A, among the light reflected from the living body 100 is received in the first light receiving element 20A, and the light, having passed through the second filter 21B, is received in the second light receiving element 20B. In this embodiment of the invention, the wavelength of the light having passed through the first filter 21A is equal to the wavelength of the light having passed through the second filter 21B.

An amplifying unit 22 includes an inverting amplifying circuit using an operational amplifier, and is composed of an operational amplifier OP and a resistor R. Specifically, one terminal of the resistor R is connected to an output terminal of the operational amplifier OP, and the other terminal of the resistor R is connected to an inverting input terminal and a connection point of an anode of the first light receiving element 20A and a cathode of the second light receiving element 20B. Also, the output terminal of the operational amplifier OP is connected to an analog-to-digital (A/D) converter 23. To the non-inverting input terminal of the operational amplifier OP, a predetermined voltage is applied.

The A/D converter 23 connected to the control unit 30 is provided with a circuit that converts an analog signal into a digital signal. The A/D converter 23 converts an analog signal output from the output terminal of the operational amplifier OP into a digital signal, and outputs the digital signal to the control unit 30.

1-3. Operation

First, if power from a power supply (not illustrated) is supplied to the respective units of the measuring apparatus 1, a control program stored in the ROM starts to be executed by the control unit 30. If a manipulation that assigns a start of measurement of the pulse or pulse wave is performed in the manipulation unit 50 after the start of the control program, the switch 11 is closed by the control unit 30. If the switch 11 is closed, current flows through the light source 10, and light α is output from the light source 10. The light α output from the light source 10 is reflected within a blood vessel of the living body 100, and the reflected light α1 reaches the first filter 21A. Also, light β, such as light from light equipment, sunlight, and the like, which is not the light that is output from the light source 10, reaches the living body 100. If the light β is reflected within the blood vessel of the living body 100, the reflected light β1 reaches the first filter 21A and the second filter 21B.

Here, the first filter 21A transmits the light of a wavelength λ that is included in the light α1 (i.e. a first reflected light) and the light of the wavelength λ that is included in the light β1 (i.e. a second reflected light). If the transmitted light reaches the first light receiving element 20A, current according to the transmitted light flows to the first light receiving element 20A. Since the light from the light α1 and the light from the light β1 reach the first light receiving element 20A, the current Ia flowing through the first light receiving element 20A includes a current component Ia1 that flows by the light from the light α1 and a current component Ia2 that flows by the light from the light β1. On the other hand, the second filter 21B transmits light of the wavelength λ (a third reflected light) included in the light β1. If the transmitted light reaches the second light receiving element 20B, the current Ib according to the transmitted light flows through the second light receiving element 20B.

From the viewpoint of the first light receiving element 20A and the second light receiving element 20B, the light β may be considered as the light from a point at infinity. The light β1 that reaches the first light receiving element 20A has the same light quantity as the light β1 that reaches the second light receiving element 20B. Accordingly, the current component Ia2 flowing in the first light receiving element 20A by the light β1 among the current Ia becomes equal to the current Ib flowing in the second light receiving element 20B by the light β1. Between the anode of the first light receiving element 20A and the cathode of the second light receiving element 20B, a voltage E according to a difference between the current Ia flowing in the first light receiving element 20A and the current Ib flowing in the second light receiving element 20B, i.e. according to the current component Ia1 that flows by the light from the light α1, is obtained. The voltage E is amplified by the amplifying unit 22, and then is converted into a digital signal by the A/D converter 23. The converted digital signal is input to the control unit 30. The control unit 30 obtains the pulse or pulse wave by analyzing the input digital signal, and controls the display unit 40 to display the pulse or pulse wave. That is, the control unit 30 functions as an information generating unit that generates information on the living body. In the case of the configuration that is not provided with the second light receiving element 20B, the first filter 21A, and the second filter 21B, the light α1 and the light β1 reach the first light receiving element 20A, and the voltage amplified by the amplifying unit 22 includes a voltage component obtained from the light α1 and a voltage component obtained from the light β1. In this embodiment of the invention, the voltage component by the light β1 is excluded from the signal amplified by the amplifying unit 22, and only the voltage component obtained from the light α1 which is output from the light source 10 and is reflected within the blood vessel is amplified by the amplifying unit 22. Accordingly, the pulse waveform obtained by the control unit 30 is displayed with higher accuracy.

1-4. Modified Example

The first embodiment may be modified as follows.
The light source 10 may be a light emitting diode that emit light having a plurality of wavelengths, being so called a white light emitting diode. In this case, between the light source 10 and the living body 100, a filter (i.e. second filter) that transmits light having the same wavelength as that of the light transmitted through the first filter 21A and the second filter 21B may be arranged, and the living body 100 may be irradiated only with the light having a predetermined wavelength. According to this configuration, since the living body 100 is irradiated with the light of a single wavelength and the light having the same wavelength as the light with which the living body is irradiated is received in the first light receiving element 20A, the measurement can be performed with high accuracy. Also, in this embodiment of the invention, the light source 10 is composed of a light emitting diode. However, the light source 10 may also be a laser element that outputs laser light.

In order to prevent the light α1 which is output from the light source 10 and is reflected from the living body 100 from reaching the second light receiving element 20B, a member which shades the light which is output from the light source 10 and is reflected from the living body 100 may be arranged around the second light receiving element 20B. Also, in order to prevent the light, such as the light from illumination equipment or the sunlight, which is not output from the light source 10, from directly reaching the first light receiving element 20A and the second light receiving element 20B, members that shade the corresponding light may be arranged around the respective light receiving elements.

The first filter 21A and the second filter 21B may be formed integrally. Also, the first filter 21A and the second filter 21B may be filters that can vary the wavelength of the transmitted light. For example, the first filter and the second filter may be variable filters that change the wavelength of the transmitted light in accordance with an applied driving voltage as described in JP-A-2005-24825. According to this construction, it is possible to change the wavelength of light with which the living body is irradiated and which is reflected from the living body, and thus the measurement can be performed with high accuracy through selection of the wavelength of the light with which the living body is irradiated according to the living body.

Figure 4:
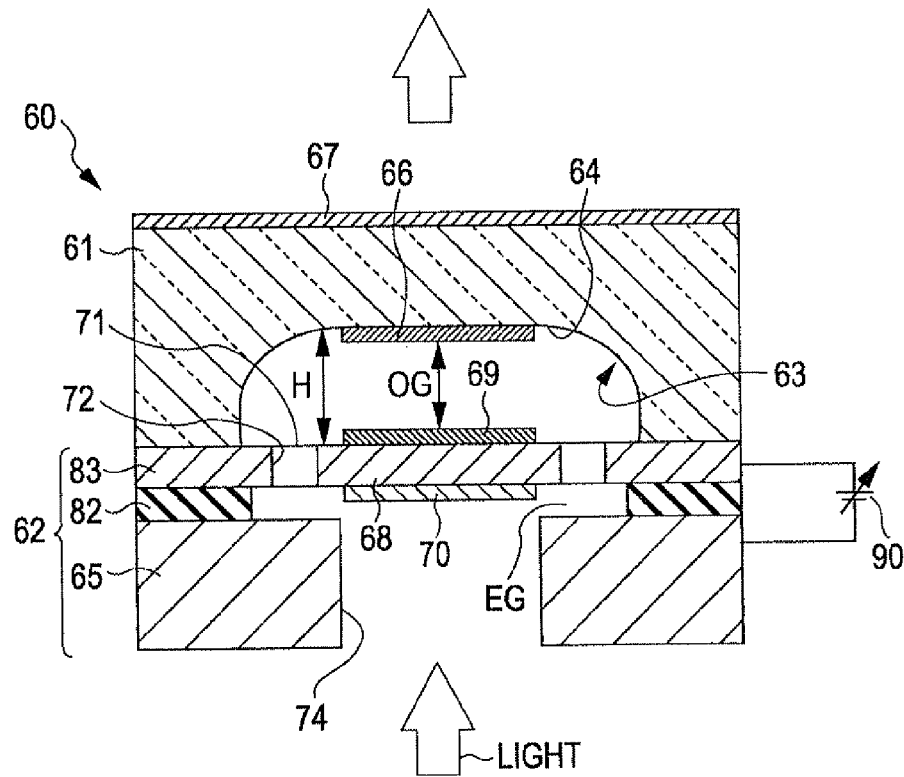
FIG. 4 is a view illustrating the configuration of filter according to a modified example of the first embodiment of the invention.

FIG. 4 is a view illustrating the cross section of a variable filter 60. A first substrate 61 is a glass substrate, and the second substrate 62 is a silicon on insulator (SOI) substrate. The first substrate 61 and the second substrate 62 form bipolar junction. The first substrate 61 has a recessed part 63 having a depth H. The bottom surface 64 of the recessed part is flat and smooth. On the bottom surface 64 of the recessed part, a reflective film 66, which is obtained by alternately laminating an $SiO_2$ film and a $Ta_2O_5$ film, is formed. On an opposite side of the bottom surface 64 of the first substrate 61, an anti-reflective film 67, which is obtained by alternately laminating an $SiO_2$ film and a $Ta_2O_5$ film, is formed. The second substrate 62 has a structure in which a support substrate 65, an insulating layer (e.g. $SiO_2$ film) 82, and an Si active layer 83 are laminated. On the active layer 83, a reflective film 69 that is opposite to the reflective film 66, a moving part 68 having an anti-reflective film 70, and a hinge part 71 are formed. The reflective film 69 has the same construction as the reflective film 66. The anti-reflective film 70 has the same construction as the anti-reflective film 67. The hinge part 71 supports the moving part 68 and has elasticity. On the second substrate 62, a through-hole 74 and an electrostatic gap EG are formed. In the second substrate 62, the active layer 83 is laminated on the first substrate 61, and an optical gap OG is formed between the reflective film 66 and the reflective film 69. In this case, the distance H of the optical gap OG is set by an equation of interference condition of a Fabry-Perot interferometer.

In the variable filter 60, if a voltage is applied between the moving part 68 and the support substrate 65 by connecting a DC power supply 90 thereto, the moving part 68 is charged into the plus polarity and the support substrate 70 is charged into the minus polarity. Accordingly, electrostatic attraction occurs therebetween to make the moving part 68 be pulled near the support substrate 70. The elastic hinge part 71 is bent, and the moving part 68 is displaced in parallel while it maintains its horizontal state. In this case, the position of the moving part 68 can be changed by changing the applied voltage. Here, if the light is incident from the though-hole 74 vertically to the moving part 68, the incident light is transmitted through the moving part 68, and repeats reflection in a space between the reflective film 66 and the reflective film 69. Here, only the light having a wavelength that satisfies the interference condition determined by the distance H is transmitted through the first substrate 61. If the applied voltage is changed, the distance H of the variable filter 60 is changed to change the interference condition. Accordingly, by controlling the applied voltage, the wavelength of the transmitted light can be changed.

Figure 3:
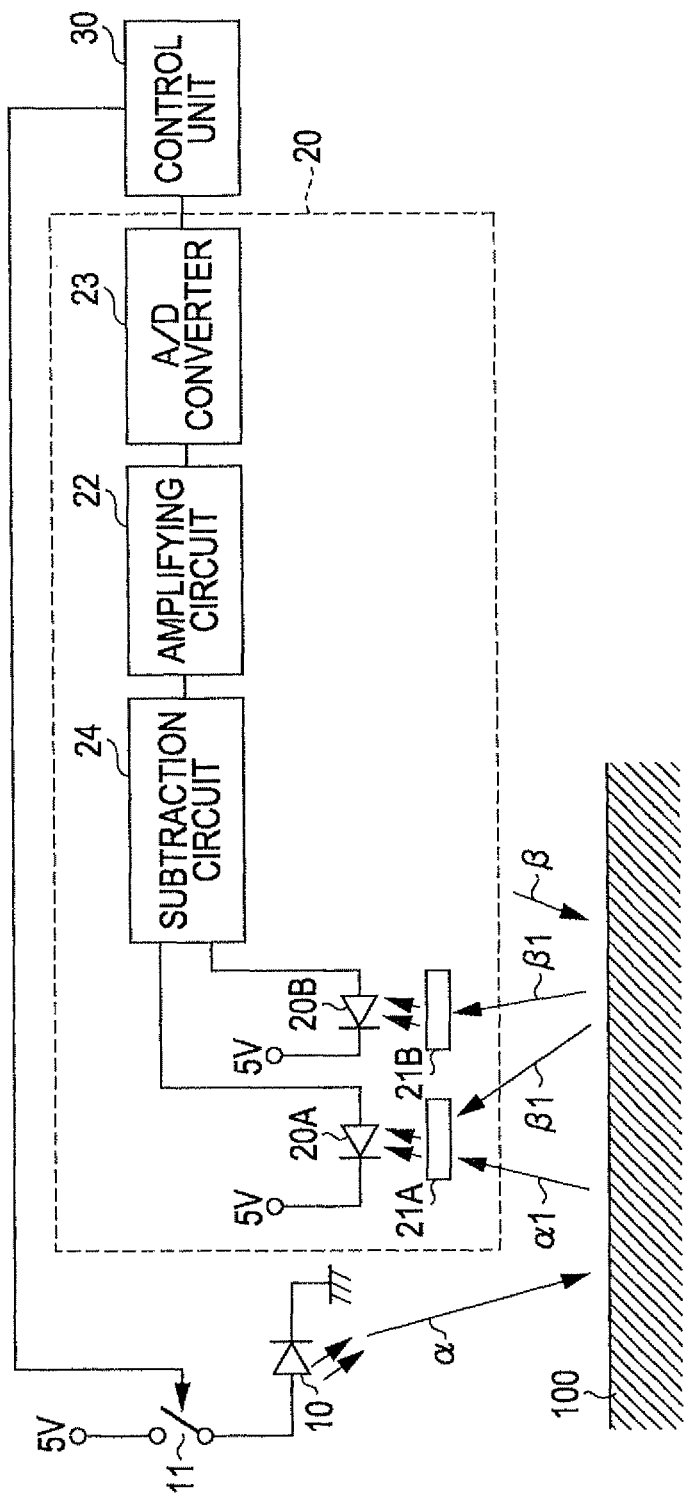
FIG. 3 is a view illustrating the electrical configuration of a measuring apparatus according to a modified example of the first embodiment of the invention.

As illustrated in FIG. 3, it is also possible that the first light receiving element 20A and the second light receiving element 20B are not connected in series, but a subtraction circuit 24 is installed to subtract a signal sent through the second light receiving element 20B from a signal sent through the first light receiving element 20A, and the result of subtraction is amplified by the amplifying unit 22.

2. Second Embodiment

2-1. Whole Construction

Figure 5:
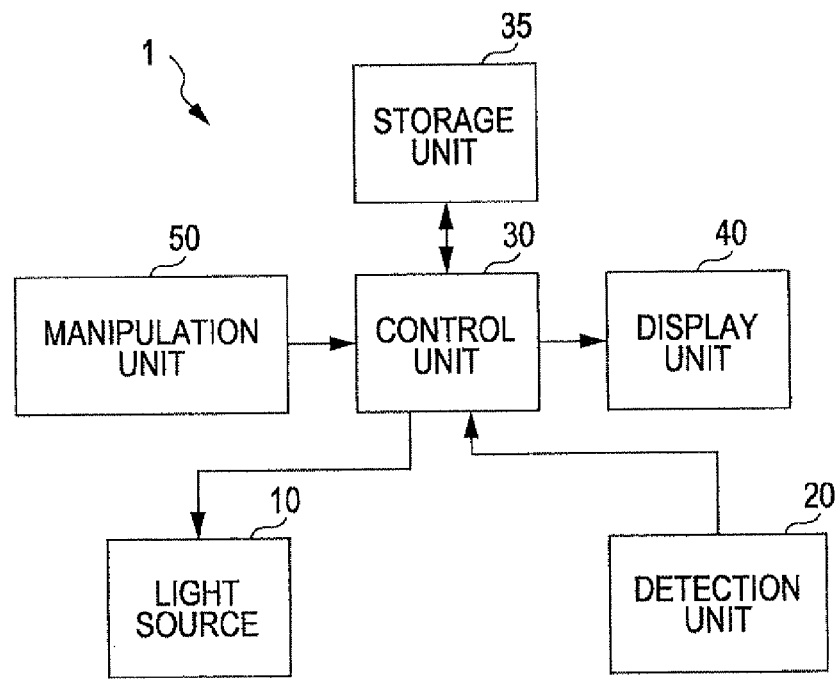
FIG. 5 is a block diagram illustrating the hardware configuration of a measuring apparatus according to a second embodiment of the invention.

FIG. 5 is a block diagram illustrating the configuration of a measuring apparatus 2 according to an embodiment of the invention. The measuring apparatus 2 is an apparatus for measuring the pulse or pulse wave of a living body (i.e. an object to be measured). The measuring apparatus 2 includes a light source 10, a detection unit 20, a control unit 30, a storage unit 35, a display unit 40, and a manipulation unit 50. In this case, common reference numerals are used for common constituent elements as in the first embodiment of the invention.

The storage unit 35 is a nonvolatile memory, and is connected to the control unit 30. The storage unit 35, under the control of the control unit 30, stores signals output from the detection unit 20.

2-2. Electrical Configuration

Figure 6:
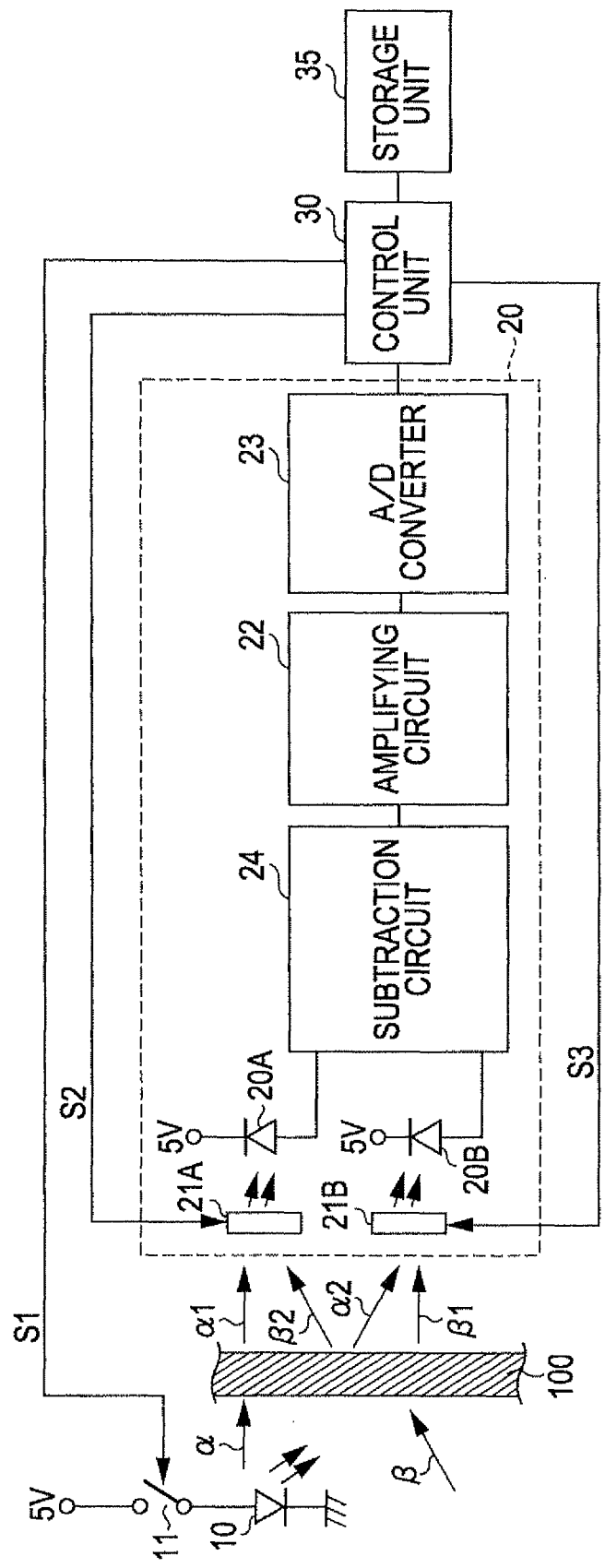
FIG. 6 is a view illustrating the electrical configuration of a light source and a detection unit.

FIG. 6 is a view illustrating the electrical configuration of the light source 10 and the detection unit 20. In this embodiment of the invention, the light source 10 is a light emitting diode that outputs light of a predetermined single wavelength, and the wavelength λ of the light output from the light source 10 is within a near-infrared range (e.g. 700 nm to 1200 nm). The switch 11 connected to the power supply is connected to the light source 10. The switch 11 is switched to an open/close state by a signal S1 from the control unit 30 to turn on/off the light source 10.

The first light receiving element 20A and the second light receiving element 20B are all reverse-biased, and anodes thereof are connected to a subtraction circuit 24. In this embodiment of the invention, the first filter 21A and the second filter 21B are filters in which the wavelength of the transmitted light is changed by the control from an outside. In this embodiment of the invention, for example, the filters are variable filters (See FIG. 4) that change the wavelength of the transmitted light in accordance with the applied voltage as described in JP-A-2005-24825.

The subtraction circuit 24 (i.e. a difference extracting unit) is a subtraction circuit using an operational amplifier. The subtraction circuit 24 subtracts the signal from the second light receiving element 20B from the signal from the first light receiving element 20A, and outputs a signal obtained by the subtraction to the amplifying circuit 22. The amplifying circuit 22 is provided with an inverting amplifying circuit using an operational amplifier, and amplifies the signal input from the subtraction circuit 24 to output the amplified signal to the A/D converter 23.

2-3. Operation

Figure 7:
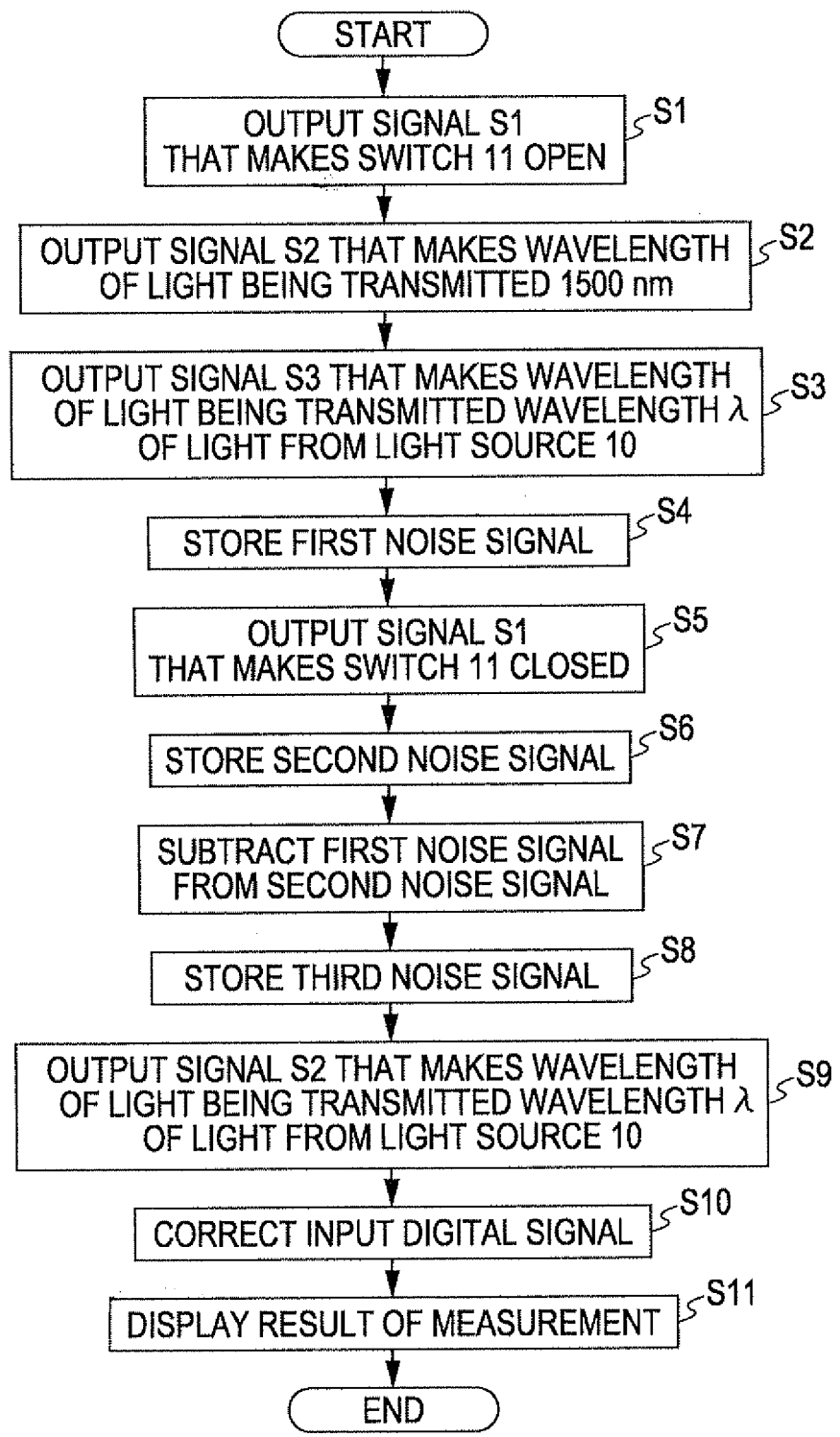
FIG. 7 is a flowchart illustrating a flow of processes performed by a control unit.

First, if power from a power supply (not illustrated) is supplied to the respective units of the measuring apparatus 2, a control program stored in the ROM starts to be executed in the control unit 30. If a manipulation that assigns a start of measurement of the pulse or pulse wave is performed in the manipulation unit 50 after the start of the control program, the switch 11 is opened (step S1 in FIG. 7) by a signal S1 output from the control unit 30. In this case, since no current flow from the power supply to the light source 10, the light source 10 is turned off.

Then, the control unit 30 controls the voltage applied from a DC power supply 90 to the first filter 21A by controlling the DC power supply 90 connected to the first filter 21A with the signal S2, and makes the wavelength of the light transmitted through the first filter 21A be 1500 nm (step S2). The light having a wavelength larger than that of the near-infrared range (of 700 nm to 1200 nm) is absorbed into water inside the living body 100. Accordingly, it is difficult for the light having a wavelength of equal to more than 1500 nm to pass through the living body 100, and thus the light does not reach the first filter 21A. Also, the light having a wavelength of less than 1500 nm reaches the first filter 21A, but is intercepted by the first filter 21A, and thus the light receiving part of the first light receiving element 20A is in a dark state in which no light reaches.

Then, the control unit 30 controls the voltage applied from the DC power supply 90 to the second filter 21B by controlling the DC power supply 90 connected to the second filter 21B with the signal S3, and makes the wavelength of the light transmitted through the second filter 21B have the wavelength λ of the light output from the light source 10 (step S3). Here, the light β, such as the light from illumination equipment or the sunlight (hereinafter referred to as "external light"), which is not the light output from the light source 10 (and may be considered as light from a point at infinity), reaches the living body 100, the light having a wavelength equal to or more than 1500 nm is not transmitted through the living body 100. The light β having a wavelength in a near-infrared range, which has been transmitted through the living body 100, reaches the first filter 21A. The light β1, which has been transmitted through the first filter 21A, reaches the second filter 21B.

In the first filter 21A, the wavelength of the transmitted light is 1500 nm. Since the light β2 is not transmitted through the first filter 21A, the light β2 makes no current flow in the first light receiving element 20A. On the other hand, in the second filter 21B, the light of a wavelength λ included in the light β1 is transmitted through the second filter 21B. If the transmitted light reaches the second light receiving element 20B, current Iβ1 according to the transmitted light β1 flows in the second light receiving element 20B.

A signal from the first light receiving element 20A and a signal from the second light receiving element 20B are input to the subtraction circuit 24. The subtraction circuit 24 subtracts the signal of the second light receiving element 20B from the signal of the first light receiving element 20A. A signal obtained by the subtraction is amplified by the amplifying circuit 22, and then is converted into a digital signal by the A/D converter 23. The digital signal is input to the control unit 30. The digital signal input to the control signal 30 corresponds to the light β1 that is the external light, i.e. the light that is different from the light which is output from the light source 10 and is transmitted through the living body 100, and becomes a noise signal when the pulse or pulse wave is measured. The control unit 30 stores the input digital signal in the storage unit 35 as a first noise signal (step S4).

Then, the control unit 30 outputs the signal S1 to close the switch 11 (step S5). Then, the switch 11 is closed to make current flow to the light source 10, and the light source 10 is turned on to irradiate the living body 100 with the light a having a wavelength λ. The light α1, which has been transmitted through the living body 100, among the light α reaches the first filter 21A, and a scattered light α2, which is output form the light source 10 and is transmitted through the living body 100, reaches the second filter 21B. Also, if the light β, which is the external light, reaches the living body 100, the light β2, which has been transmitted through the living body 100, among the light β from a point at infinity reaches the first filter 21A, and the transmitted light β1 reaches the second filter 21B.

In the first filter 21A, the wavelength of the transmitted light is 1500 nm, and the light α1 and the light β2 are not transmitted through the first filter 21. Accordingly, no current flows by the light α1 and the light β2 in the first light receiving element 20A. On the other hand, the light of a wavelength λ included in the scattered light α2 is transmitted through the second filter 21B, and the light of a wavelength λ included in the light β1 is transmitted through the second filter 21B. If the transmitted light reaches the second light receiving element 20B, the current according to the transmitted light flows in the second light receiving element 20B.

The subtraction circuit 24 subtracts the signal of the second light receiving element 20B from the signal of the first light receiving element 20A. The signal obtained by the subtraction is amplified by the amplifying circuit 22, and then is converted into a digital signal by the A/D converter 23. The digital signal is input to the control unit 30. The digital signal input to the control signal 30 corresponds to the scattered light α2 and the light β1, which become a noise signal when the pulse or pulse wave is measured. The control unit 30 stores the input digital signal in the storage unit 35 as a second noise signal (step S6).

Then, the control unit 30 performs a subtraction process between the first noise signal and the second noise signal stored in the storage unit 35 (step S7). Here, since the first noise signal includes the component of the light β1 and the second noise signal includes the components of the scattered light α2 and the light β1, the component of the light α2 in the noise signal can be obtained by subtracting the first noise signal from the second noise signal. If the component of the scattered light α2 is obtained by the subtraction operation, the control unit 30 stores a third noise signal that indicates the component of the scattered light α2 in the storage unit 35 (step S8).

Then, the control unit 30 starts the measurement of the living body 100. First, the control unit 30 controls the DC power supply 90 connected to the first filter 21A with the signal S2. Specifically, the control unit 30 controls the voltage applied from the DC power supply 90 to the first filter 21A to make the wavelength of the light that is transmitted through the first filter 21A have the wavelength λ of the light output from the light source 10 (step S9).

Here, the light α1 transmitted through the living body 100 among the light α reaches the first filter 21A, and the scattered light α2 transmitted through the living body 100 among the light α2 reaches the second filter 21B. Also, the light β2 transmitted through the living body 100 among the light β from a point at infinity as an external light reaches the first filter 21A, and the light β1 reaches the second filter 21B.

The light of a wavelength λ included in the light α1 and the light of a wavelength λ included in the light β2 are transmitted through the first filter 21A. If the transmitted light reaches the first light receiving element 20A, the current Ia according to the transmitted light flows in the first light receiving element 20A. Here, the current Ia includes the current component Iα1 that flows by the light α1 and the current component Iβ2 that flows by the light β2. Also, the light of a wavelength λ included in the scattered light α2 and the light of a wavelength λ included in the light β1 are transmitted through the second filter 21B. If the transmitted light reaches the second light receiving element 20B, the current Ib according to the transmitted light flows in the second light receiving element 20B. Here, the current Ib includes the current component Iα2 that flows by the light α2 and the current component Iβ1 that flows by the light β1.

Here, the signal output from the subtraction circuit 24 to the amplifying circuit 22 becomes the difference between the current Ia flowing in the first light receiving element 20A and the current Ib flowing in the second light receiving element 20B. This signal is amplified by the amplifying circuit 22, and then is converted into a digital signal by the A/D converter 23. The digital signal is input to the control unit 30. Since the light β2 reaching the first light receiving element 20A and the light β1 reaching the second light receiving element 20B are lights from a point at infinity and can approximate the same light, the signal traveling in the amplifying circuit 22 becomes the difference between the current Iα1 and the current Iα2.

If the digital signal is input from the A/D converter 23, the control unit 30 reads out the third noise signal that indicates the component of the scattered light α2 from the storage unit 35. In order to correct the influence of the scattered light α2 in the input digital signal, the control unit 30 corrects the digital signal input from the A/D converter 23 using the third noise signal (step S10). The control unit 30 obtains the pulse or pulse wave by analyzing the digital signal obtained by the correction. After the pulse waveform is obtained, the control unit 30 controls the display unit 40 to display the pulse or pulse waveform (step S11). That is, the control unit 30 functions as the information generating unit that generates information on the living body.

In this embodiment of the invention, the component by the light β is excluded from the signal amplified by the amplifying circuit 22, and the influence of the scattered light α2 is corrected by the control unit 30. Accordingly, the pulse waveform obtained by the control unit 30 is displayed with higher accuracy.

2-4. Modified Example

The second embodiment may be modified as follows. Also, the modified example of the first embodiment may be applied to the second embodiment of the invention.

The light source 10 may be a light emitting diode that emit light having a plurality of wavelengths, being so called a white light emitting diode. In this case, between the light source 10 and the living body 100, a third filter that is identical to the first filter 21A and the second filter 21B (i.e. a third filter) may be arranged, and the living body 100 may be irradiated only with the light having a predetermined wavelength by controlling the third filter through the control unit 30. According to this configuration, the living body 100 is irradiated with the light of a single wavelength, and thus the measurement can be performed with high accuracy.

Figure 8:
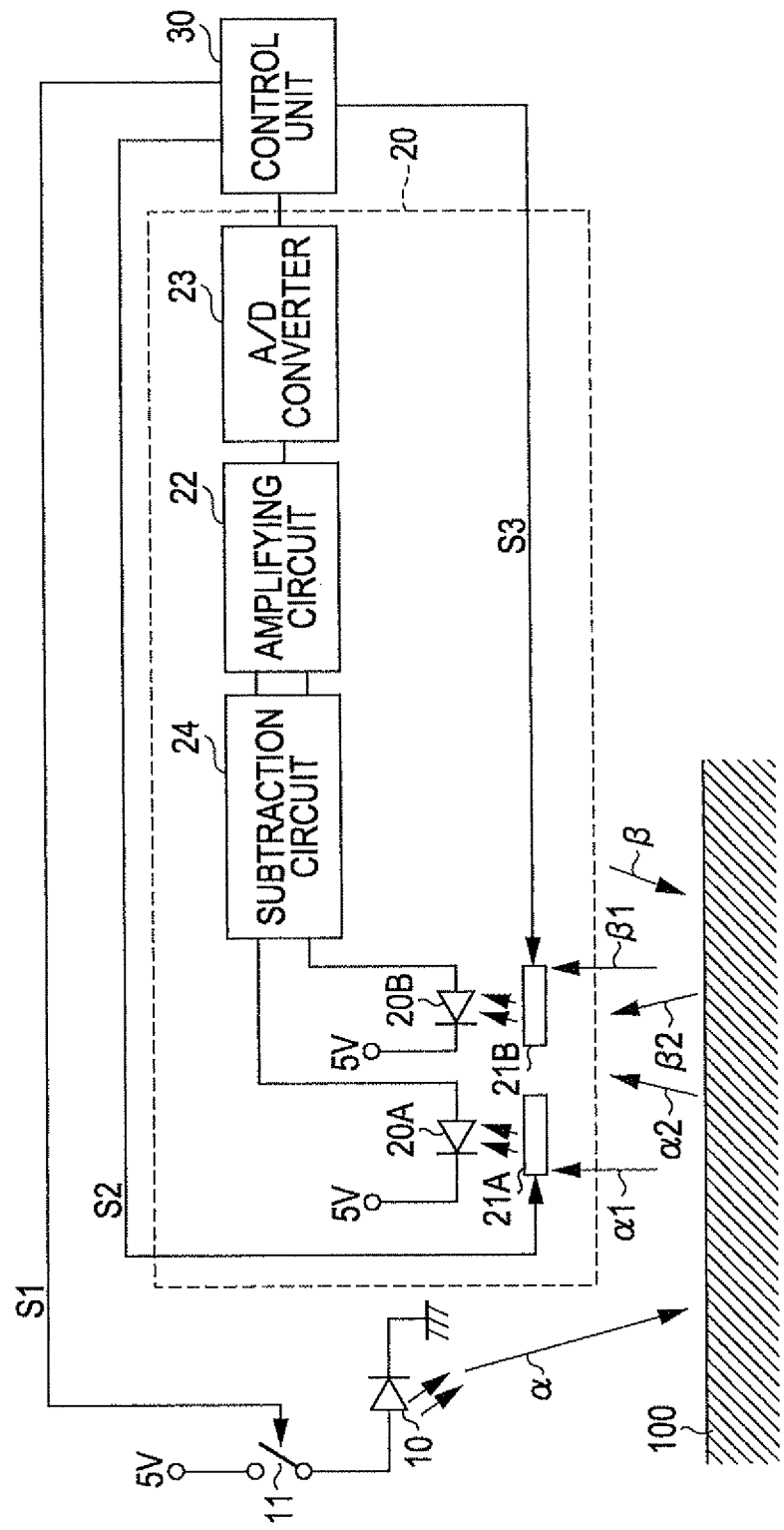
FIG. 8 is a view illustrating the electrical configuration of a measuring apparatus according to a modified example of the second embodiment of the invention.

The measuring apparatus 2, as illustrated in FIG. 8, may have the configuration in which the living body 100 is irradiated with the light from the light source 10 and the light reflected in the blood vessel of the living body 100 is detected.

Figure 9:
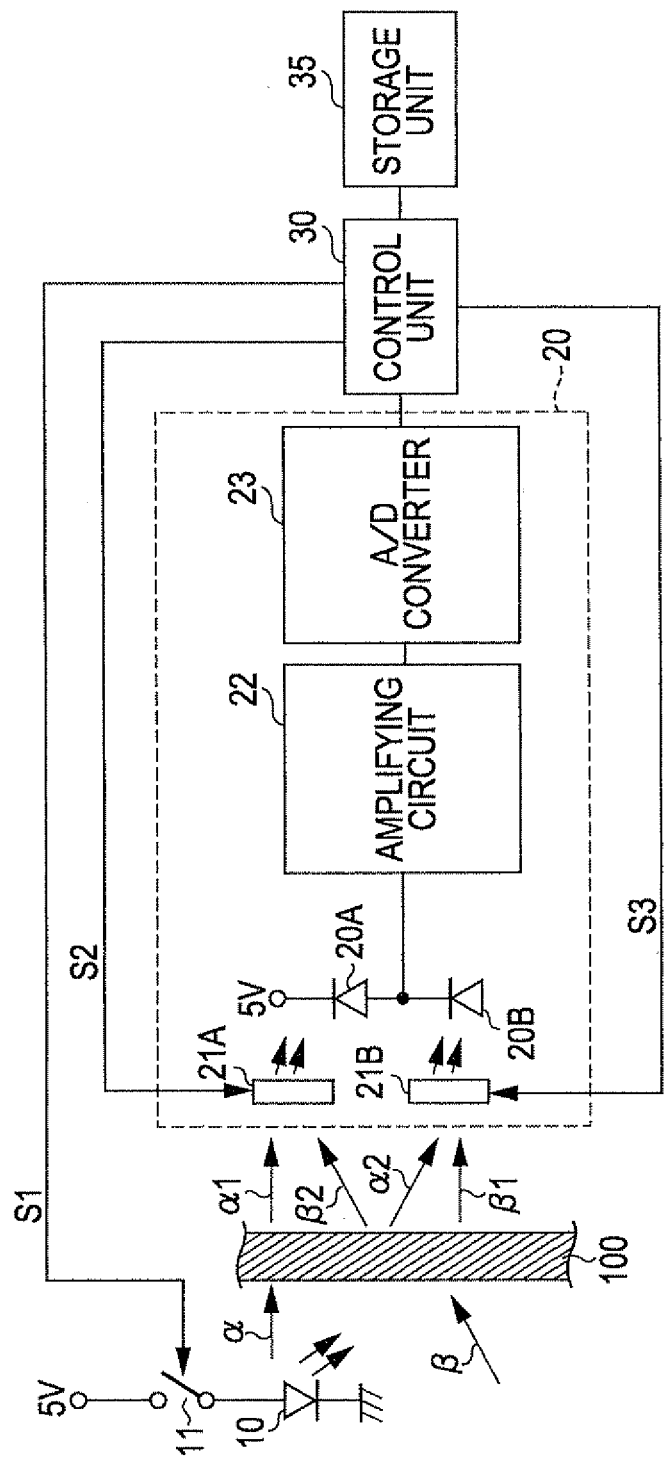
FIG. 9 is a view illustrating the electrical configuration of a measuring apparatus according to a modified example of the second embodiment of the invention.

As illustrated in FIG. 9, the first light receiving element 20A and the second light receiving element 20B may be connected in series, and the signal that travels between the first light receiving element and the second light receiving element may be amplified by the amplifying circuit 22.

The wavelength of the light transmitted through the first filter 21A is not limited to that as described above in the embodiments of the invention, and any different wavelength that is larger than that of the near-infrared range may be used.

If the second filter 21B is a filter that transmits light having the same wavelength as the light output from the light source 10, it may not be a filter that can change the wavelength of light.

The measuring apparatus 2 may have the configuration in which the signal output from the first light receiving element 20A is amplified and A/D-converted, the signal output from the second light receiving element 20B is amplified and A/D-converted, and the processed signals are input to the control unit 30, so that the control unit 30 performs the same subtraction process as that performed by the subtraction circuit 24 with respect to the processed signals.

3. Third Embodiment

3-1. Whole Configuration

Figure 10:
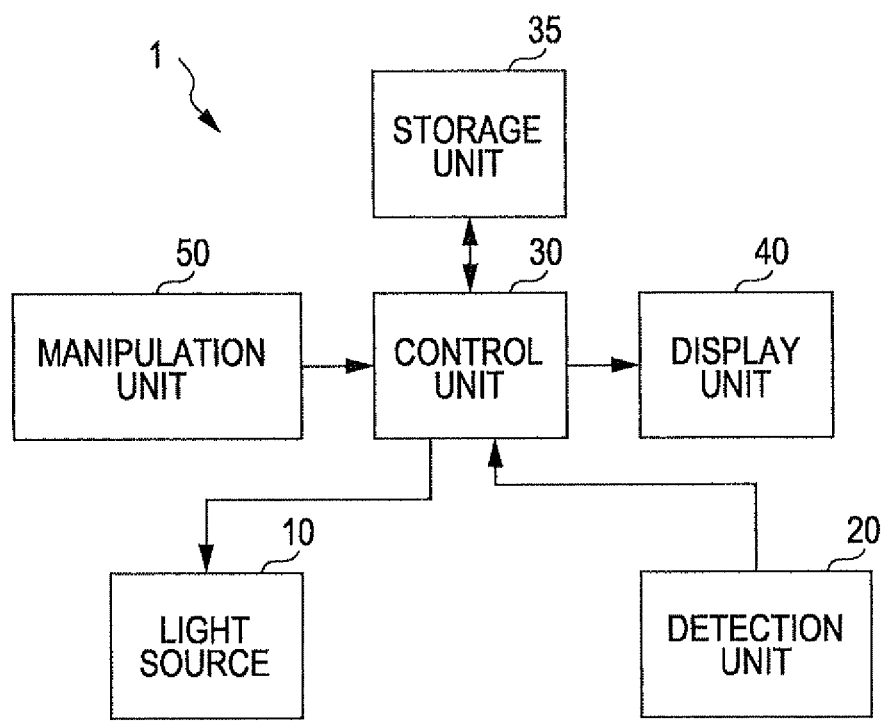
FIG. 10 is a block diagram illustrating the hardware configuration of a measuring apparatus according to a third embodiment of the invention.

FIG. 10 is a block diagram illustrating the configuration of a measuring apparatus 3 according to a third embodiment of the invention. The measuring apparatus 3 is an apparatus for measuring the pulse or pulse wave of a living body (i.e. an object to be measured). The measuring apparatus 3 includes a light source 10, a detection unit 20, a control unit 30, a storage unit 35, a display unit 40, and a manipulation unit 50. In this case, common reference numerals are used for common constituent elements as in the first or second embodiment of the invention.

3-2. Electrical Configuration

Figure 11:
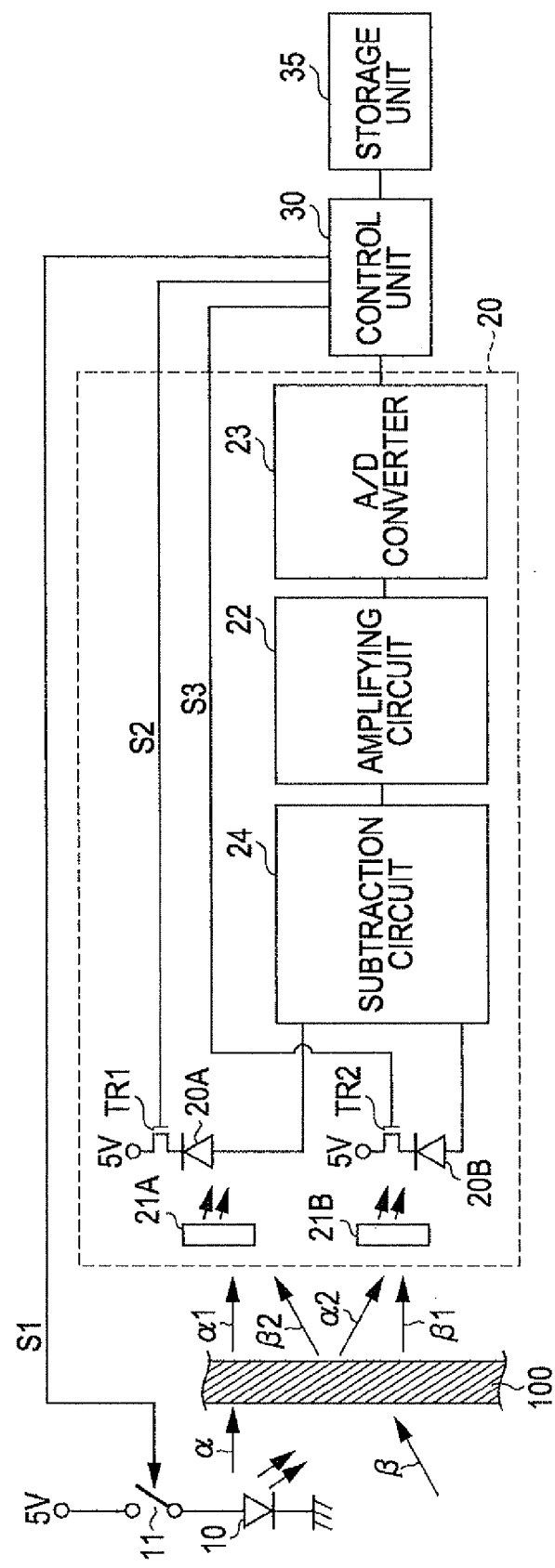
FIG. 11 is a view illustrating the electrical configuration of a light source and a detection unit.

FIG. 11 is a view illustrating the electrical configuration of the light source 10 and the detection unit 20. In this embodiment of the invention, the wavelength λ of the light output from the light source 10 is within a near-infrared range of 700 nm to 1200 nm. Anodes of the first light receiving element 20A and the second light receiving element 20B are all connected to the subtraction circuit 24. The first light receiving element 20A is reverse-biased through a first transistor TR1. The second light receiving element 20B is reverse-biased through a second transistor TR2.

The first transistor TR1 is a transistor that operates as a switch that makes current flow to the first light receiving element 20A. The first transistor TR1 has a drain connected to the power supply, a source connected to the cathode of the first light receiving element 20A, and a gate connected to the control unit 30. The first transistor TR1, if a voltage is applied to the gate by the signal S2 from the control unit 30, makes current flow to the first light receiving element 20A, while if the voltage is not applied to the gate by the signal S2, it intercepts the current flowing to the first light receiving element 20A. The second transistor TR2 is a transistor that operates as a switch that makes current flow to the second light receiving element 20B. The second transistor TR2 has a drain connected to the power supply, a source connected to the cathode of the second light receiving element 20B, and a gate connected to the control unit 30. The second transistor TR2, if a voltage is applied to the gate by the signal S3 from the control unit 30, makes current flow to the second light receiving element 20B, while if the voltage is not applied to the gate by the signal S3, it intercepts the current flowing to the second light receiving element 20B.

3-3. Operation of Embodiment

Figure 12:
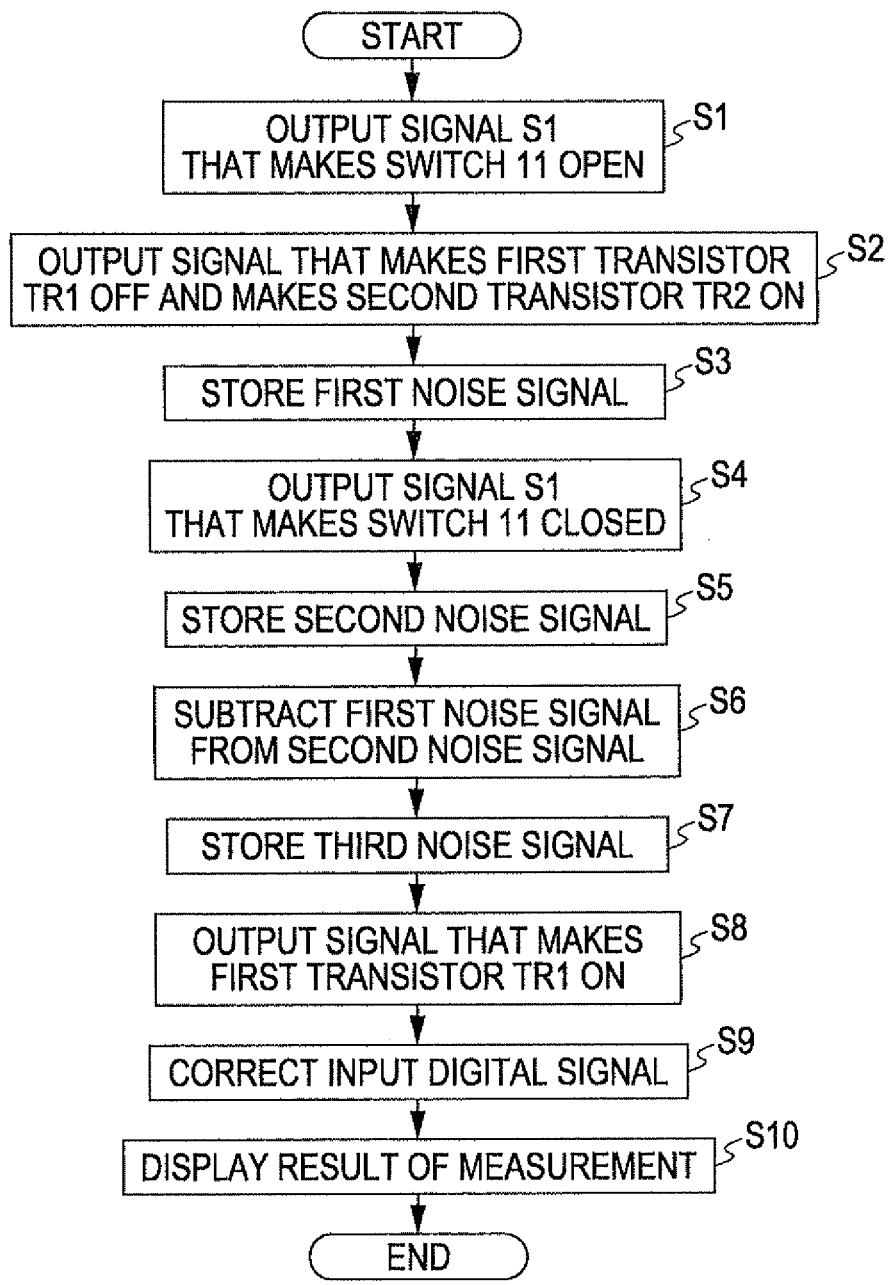
FIG. 12 is a flowchart illustrating a flow of processes performed by a control unit.

First, if power from a power supply (not illustrated) is supplied to the respective units of the measuring apparatus 3, a control program stored in the ROM starts to be executed in the control unit 30. If a manipulation that assigns the start of measurement of the pulse or pulse wave is performed in the manipulation unit 50 after the start of the control program, the switch 11 is opened (step S1 in FIG. 12) by a signal S1 output from the control unit 30. In this case, since no current flow from the power supply to the light source 10, the light source 10 is turned off.

Then, the control unit 30 makes the first transistor TR1 off by the signal S2, and makes the second transistor TR2 on by the signal S3 (step S2). If the first transistor TR1 is turned off, no current flows in the first light receiving element 20A. If the second transistor TR2 is turned on, current flows from the power supply to the second light receiving element 20B.

Here, if the light β, which is not the light output from the light source 10, reaches the living body 100, the light having a wavelength equal to or more than 1500 nm is not transmitted through the living body 100. The light β2 having a wavelength in a near-infrared range, which has been transmitted through the living body 100, reaches the first filter 21A, and the transmitted light β1 reaches the second filter 21B.

The light having a wavelength λ included in the light β2 is transmitted through the first filter 21A, and the transmitted light reaches the first light receiving element 20A. However, since the first transistor TR1 is in an off state, no current flows from the first light receiving element 20A to the subtraction circuit 24. The light having a wavelength λ included in the light β1 is transmitted through the second filter 21B. If the transmitted light reaches the second light receiving element 20B, current Iβ1 according to the transmitted light β1 flows to the subtraction circuit 24.

The subtraction circuit 24 subtracts the signal of the second light receiving element 20B from the signal of the first light receiving element 20A. The signal obtained by the subtraction is amplified by the amplifying circuit 22, and then is converted into a digital signal by the A/D converter 23. The digital signal is input to the control unit 30. The digital signal input to the control signal 30 corresponds to the external light β1, i.e. the light that is different from the light which is output from the light source 10 and is transmitted through the living body 100, and becomes a noise signal when the pulse or pulse wave as measured. The control unit 30 stores the input digital signal in the storage unit 35 as a first noise signal (step S3).

Then, the control unit 30 output a signal S1 that makes the switch 11 closed (step S4). Then, the switch 11 is closed to make the current flow to the light source 10, and thus the light source 10 is turned on to irradiate the living body 100 with the light a of a wavelength λ. Among the light α, the light α1 transmitted through the living body 100 reaches the first filter 21A, and the scattered light α2 that is output from the light source 10 and is transmitted through the living body 100 reaches the second filter 21B. Also, if the light β, which is the external light, reaches the living body 100, the light β2 transmitted through the living body 100 among the light β reaches the first filter 21A, and the transmitted light β1 reaches the second filter 21B.

Although the light having a wavelength λ included in the light α1 and the light β2 is transmitted through the first filter 21A, the first transistor TR1 is in an off state, and thus no current flows from the first light receiving element 20A to the subtraction circuit 24. The light having a wavelength λ included in the scattered light α2 and the light having a wavelength λ included in the light β1 are transmitted through the second filter 21B. If the transmitted light reaches the second light receiving element 20B, current according to the transmitted light flows to the subtraction circuit 24.

Here, the subtraction circuit 24 subtracts the signal of the second light receiving element 20B from the signal of the first light receiving element 20A. The signal obtained by the subtraction is amplified by the amplifying circuit 22, and then is converted into a digital signal by the A/D converter 23. The digital signal is input to the control unit 30. The digital signal input to the control signal 30 corresponds to the scattered light α2 and the light β1, and becomes a noise signal when the pulse or pulse wave is measured. The control unit 30 stores the input digital signal in the storage unit 35 as a second noise signal (step S5).

Then, the control unit 30 performs the subtraction between the first noise signal stored in the storage unit 35 and the second noise signal stored in the storage unit 35 (step S6). Here, the first noise signal includes the component of the light β1, and the second noise signal includes the components of the scattered light α2 and the light β1. Accordingly, by subtracting the first noise signal from the second noise signal, the component of the light α2 in the noise signal can be obtained. If the component of the scattered light α2 is obtained through the operation, the control unit 30 stores the third noise signal that indicates the component of the scattered light α2 in the storage unit 35 (step S7).

Then, the control unit 30 starts the measurement of the living body 100. First, the control unit 30 makes the first transistor TR1 on by the signal S2 (step S8). If the first transistor TR1 is turned on, current flows through the first light receiving element 20A.

Here, the light α1 transmitted through the living body 100 among the light α reaches the first filter 21A, and the scattered light α2 transmitted through the living body 100 among the light α reaches the second filter 21B. Also, the light β2 transmitted through the living body 100 among the external light β reaches the first filter 21A, and the light β1 reaches the second filter 21B.

The light of a wavelength λ included in the light α1 and the light of a wavelength λ included in the light β2 are transmitted through the first filter 21A. If the transmitted light reaches the first light receiving element 20A, the current Ia according to the transmitted light flows in the first light receiving element 20A since the first transistor TR1 is in an on state. Here, the current Ia includes the current component Iα1 that flows by the light α1 and the current component Iβ2 that flows by the light β2.

Also, the light of a wavelength λ included in the scattered light α2 and the light of a wavelength λ included in the light β1 are transmitted through the second filter 21B. If the transmitted light reaches the second light receiving element 20B, the current Ib according to the transmitted light flows in the second light receiving element 20B. Here, the current Ib includes the current component Iα2 that flows by the light α2 and the current component Iβ1 that flows by the light β1.

Here, the signal output from the subtraction circuit 24 to the amplifying circuit 22 becomes the difference between the current Ia flowing in the first light receiving element 20A and the current Ib flowing in the second light receiving element 20B. This signal is amplified by the amplifying circuit 22, and then is converted into a digital signal by the A/D converter 23. The digital signal is input to the control unit 30. If the light β2 and the light β1 are lights from a point at infinity and can approximate the same light, the light β2 reaching the first light receiving element 20A and the light β1 reaching the second light receiving element 20B are the same. The signal traveling in the amplifying circuit 22 becomes the difference between the current Iα1 and the current Iα2 since the current Iβ2 and the current Iβ1 are the same.

If the digital signal is input from the A/D converter 23, the control unit 30 reads out the third noise signal that indicates the component of the scattered light α2 from the storage unit 35. In order to correct the influence of the scattered light α2 in the input digital signal, the control unit 30 corrects the digital signal input from the A/D converter 23 using the third noise signal (step S9). The control unit 30 obtains the pulse or pulse wave by analyzing the digital signal obtained by the correction. After the pulse waveform is obtained, the control unit 30 controls the display unit 40 to display the pulse or pulse waveform (step S10). That is, the control unit 30 functions as the information generating unit that generates information on the living body.

In this embodiment of the invention, the component by the light β2 is excluded from the signal amplified by the amplifying circuit 22 and the influence of the scattered light α2 is corrected by the control unit 30. Accordingly, the pulse waveform obtained by the control unit 30 is displayed with higher accuracy.

3-4. Modified Example

The third embodiment may be modified as follows. Also, the modified example of the first embodiment or the second embodiment may be applied to the third embodiment of the invention.

Figure 13:
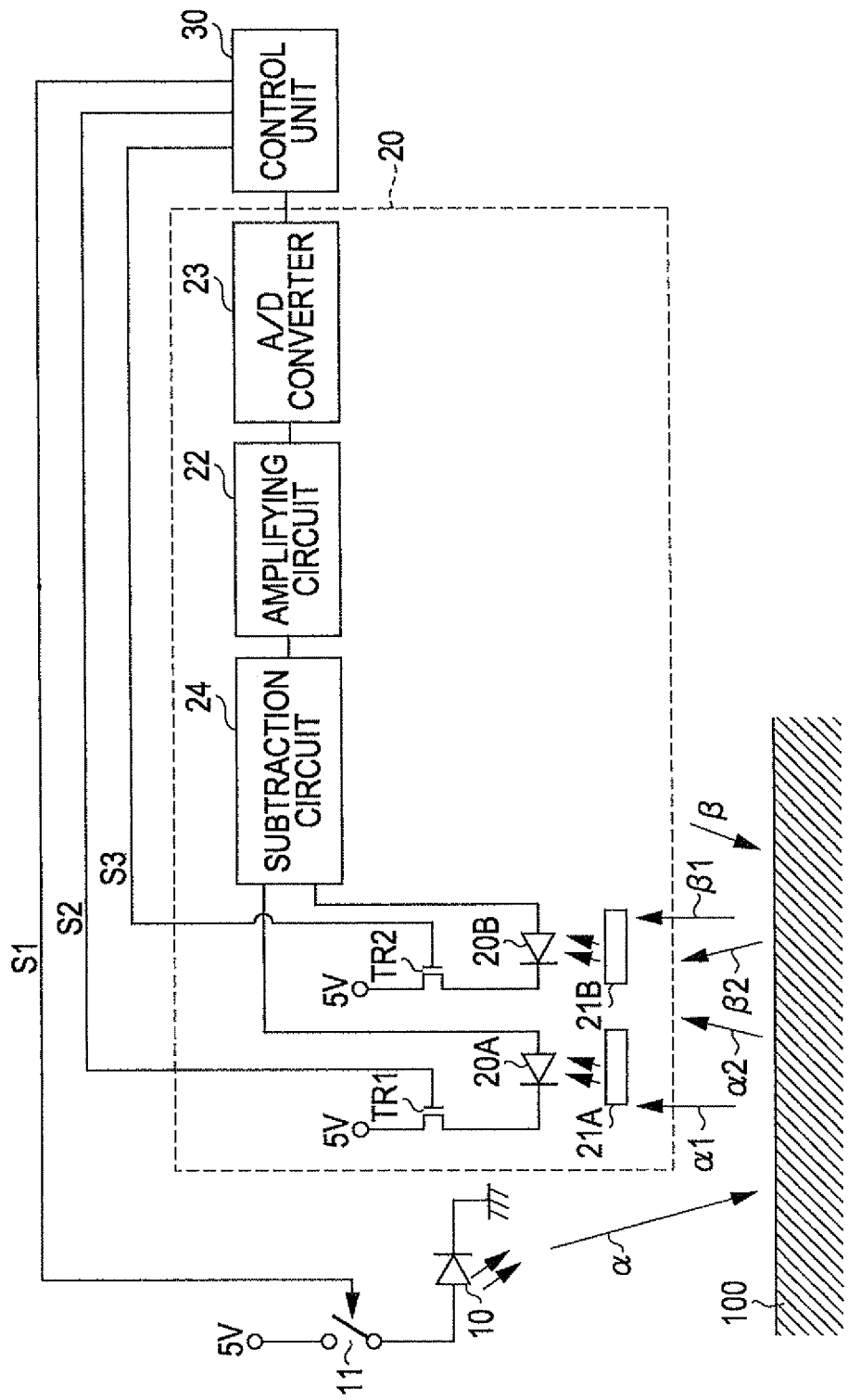
FIG. 13 is a view illustrating the electrical configuration of a measuring apparatus according to a modified example of the third embodiment of the invention.

The measuring apparatus 3, as illustrated in FIG. 13, may have the configuration in which the living body 100 is irradiated with the light from the light source 10 and the light reflected in the blood vessel of the living body 100 is detected.

The second transistor TR2 may not be installed, but the second light receiving element 20B may be reverse-biased from the power supply.

The measuring apparatuses 1 to 3 of the first to third embodiments of the invention include a filter that transmits light of a predetermined wavelength; a first light receiving unit which receives at least one of a first light that is output from a first light source (i.e. light source 10), reflected by or transmitted through an object to be measured, and transmitted through the filter and a second light that is output from a second light source (i.e. external light), reflected by or transmitted through the object to be measured, and transmitted through the filter, and through which a signal according to the received light travels; a second light receiving unit which receives light of a different path from the light received by the first light receiving unit, and through which a signal according to the received light travels; a difference extracting unit that obtains a difference signal between the signal traveling through the first light receiving unit and the signal traveling through the second light receiving unit; and an information generating unit that generates information of the object to be measured based on the signal obtained from the difference extracting unit.

What is claimed is:

1. A measuring apparatus comprising:
   a filter that transmits light of a predetermined wavelength;
   a first light receiving unit which receives a first light that is output from a first light source, reflected by or transmitted through an object to be measured, and transmitted through the filter and a second light that is output from a second light source, reflected by or transmitted through the object to be measured, and transmitted through the filter, and through which a first signal in response to the received first and second lights travels;
   a second light receiving unit which receives light of a different path from the light received by the first light receiving unit, and through which a second signal in response to the received light travels;
   a difference extracting unit that obtains a difference signal between the first signal traveling through the first light receiving unit and the second signal traveling through the second light receiving unit; and
   an information generating unit that generates information of the object to be measured based on the signal obtained from the difference extracting unit.

2. The measuring apparatus according to claim 1, wherein the first light receiving unit receives a first reflected light that is output from the first light source, reflected by the object to be measured, and transmitted through the filter and a second reflected light that is output from the second light source, reflected by the object to be measured, and transmitted through the filter; and
   the second light receiving unit receives a third reflected light that is output from the second light source, reflected by the object to be measured, and transmitted through the filter.

3. The measuring apparatus according to claim 2, further comprising:
   a second filter that transmits the light having the same wavelength as that of the light transmitted through the filter among the light output from the first light source;
   wherein the object to be measured is irradiated with the light that is output from the first light source and transmitted through the second filter.

4. The measuring apparatus according to claim 3, wherein the light output from the first light source includes light having a plurality of wavelengths, and
   the wavelength of the light that is transmitted through the filter and the second filter is changed in response to an input signal.

5. The measuring apparatus according to claim 1,
   wherein;
   the filter has a first filter and a second filter;
   the first filter transmits the light of an assigned wavelength among the light that is output from the first light source and transmitted through the object to be measured and the light that is output from the second light source and transmitted through the object to be measured;
   the second filter transmits the light of a determined wavelength among scattered light that is output from the first light source and transmitted through the object to be measured and the light that is output from the second light source and transmitted through the object to be measured;
   the first light receiving unit receives the light that is transmitted through the first filter;
   the second light receiving unit receives the light that is transmitted through the second filter;
   the measuring apparatus includes a control unit that assigns a wavelength to the first filter and controls the first light source;
   the control unit controls the first light source so that no light is output from the first light source, and stores in a storage unit the first signal that is obtained from the difference extracting unit when the wavelength that is assigned to the first filter by the control unit is longer than the wavelength of the light that is transmitted through the second filter;
   the control unit controls the first light source so that the light is output from the first light source, and stores in the storage unit the second signal that is obtained from the difference extracting unit when the wavelength that is assigned to the first filter by the control unit is longer than the wavelength of the light that is transmitted through the second filter;
   the control unit stores in the storage unit a third signal that indicates the difference between the first signal and the second signal that are stored in the storage unit;
   the control unit controls the first light source so that the light is output from the first light source, and includes a correcting unit that corrects the signal that is obtained from the difference extracting unit when the wavelength that is assigned to the first filter by the control unit is equal to the wavelength of the light that is transmitted through the second filter with the third signal that is stored in the storage unit; and
   the information generating unit generates information of the object to be measured from the signal corrected by the correcting unit.

6. The measuring apparatus according to claim 1,
   wherein the measuring apparatus includes the first light source;
   the filter has a first filter and a second filter;
   the first filter transmits the light of an assigned wavelength among the light that is output from the first light source and reflected by the object to be measured and the light that is output from the second light source and reflected by the object to be measured;
   the second filter transmits the light of a determined wavelength among scattered light that is output from the first light source and reflected by the object to be measured and the light that is output from the second light source and reflected by the object to be measured;
   the first light receiving unit receives the light that is transmitted through the first filter;
   the second light receiving unit receives the light that is transmitted through the second filter;
   the measuring apparatus includes a control unit that assigns a wavelength to the first filter and controls the first light source;
   the control unit controls the first light source so that no light is output from the first light source, and stores in a storage unit the first signal that is obtained from the difference extracting unit when the wavelength that is assigned to the first filter by the control unit is longer than the wavelength of the light that is transmitted through the second filter;
   the control unit controls the first light source so that the light is output from the first light source, and stores in the storage unit the second signal that is obtained from the difference extracting unit when the wavelength that is assigned to the first filter by the control unit is longer than the wavelength of the light that is transmitted through the second filter;

the control unit stores in the storage unit a third signal that indicates the difference between the first signal and the second signal that are stored in the storage unit;

the control unit controls the first light source so that the light is output from the first light source, and includes a correcting unit that corrects the signal that is obtained from the difference extracting unit when the wavelength that is assigned to the first filter by the control unit is equal to the wavelength of the light that is transmitted through the second filter with the third signal that is stored in the storage unit; and the information generating unit generates information of the object to be measured from the signal corrected by the correcting unit.

7. The measuring apparatus according to claim 5, further comprising:

a third filter that transmits light of a predetermined wavelength;

wherein the wavelength of the light transmitted through the second filter is equal to the wavelength of the light transmitted through the third filter; and the light output from the first light source is transmitted through the third filter and output to the object to be measured.

8. The measuring apparatus according to claim 6, further comprising:

a third filter that transmits light of a predetermined wavelength;

wherein the wavelength of the light transmitted through the second filter is equal to the wavelength of the light transmitted through the third filter; and the light output from the first light source is transmitted through the third filter and output to the object to be measured.

9. The measuring apparatus according to claim 1, wherein the light output from the first light source includes light having a plurality of wavelengths.

10. The measuring apparatus according to claim 1, wherein;

the first light receiving unit receives measuring light that is output from the first light source, transmitted through the object to be measured, and then transmitted through the filter and the light that is output from the second light source, transmitted through the object to be measured, and then transmitted through the filter; and the second light receiving unit receives scattered light that is output from the first light source, transmitted through the object to be measured, and then transmitted through the filter and the light that is output from the second light source, transmitted through the object to be measured, and then transmitted through the filter;

the measuring apparatus includes a control unit that controls the first light source and the first light receiving unit;

the control unit controls the first light source so that no light is output from the first light source, and stores in a storage unit the first signal that is obtained from the difference extracting unit when the first light receiving unit is controlled by the control unit so that the first light receiving unit does not respond to the light;

the control unit controls the first light source so that the light is output from the first light source, and stores in the storage unit the second signal that is obtained from the difference extracting unit when the first light receiving unit is controlled by the control unit so that the first light receiving unit does not respond to the light;

the control unit stores in the storage unit a third signal that indicates the difference between the first signal and the second signal that are stored in the storage unit;

the control unit controls the first light source so that the light is output from the first light source, and includes a correcting unit that corrects the signal that is obtained from the difference extracting unit when the first light receiving unit is controlled by the control unit so that the first light receiving unit responds to the light with the third signal that is stored in the storage unit; and the information generating unit generates information of the object to be measured from the signal corrected by the correcting unit.

11. The measuring apparatus according to claim 1, wherein the measuring apparatus includes the first light source;

the first light receiving unit receives measuring light that is output from the first light source, reflected by the object to be measured, and then transmitted through the filter and the light that is output from the second light source, reflected by the object to be measured, and then transmitted through the filter;

the second light receiving unit receives scattered light that is output from the first light source, reflected by the object to be measured, and then transmitted through the filter and the light that is output from the second light source, reflected by the object to be measured, and then transmitted through the filter;

the measuring apparatus includes a control unit that controls the first light source and the first light receiving unit;

the control unit controls the first light source so that no light is output from the first light source, and stores in a storage unit the first signal that is obtained from the difference extracting unit when the first light receiving unit is controlled by the control unit so that the first light receiving unit does not respond to the light;

the control unit controls the first light source so that the light is output from the first light source, and stores in the storage unit the second signal that is obtained from the difference extracting unit when the first light receiving unit is controlled by the control unit so that the first light receiving unit does not respond to the light;

the control unit stores in the storage unit, a third signal that indicates the difference between the first signal and the second signal that are stored in the storage unit;

the control unit controls the first light source so that the light is output from the first light source, and includes a correcting unit that corrects the signal that is obtained from the difference extracting unit when the first light receiving unit is controlled by the control unit so that the first light receiving unit responds to the light with the third signal that is stored in the storage unit; and the information generating unit generates information of the object to be measured from the signal corrected by the correcting unit.

12. The measuring apparatus according to claim 10, further comprising:

a second filter that transmits the light having the same wavelength as that of the light transmitted through the filter;

wherein the object to be measured is irradiated with the light that is output from the first light source and transmitted through the second filter.

13. The measuring apparatus according to claim 11, further comprising:
a second filter that transmits the light having the same wavelength as that of the light transmitted through the filter;
wherein the object to be measured is irradiated with the light that is output from the first light source and transmitted through the second filter.

14. A measuring method comprising:
receiving a first light that is output from a first light source, reflected by or transmitted through an object to be measured, and transmitted through a filter that transmits light of a predetermined wavelength and a second light that is output from a second light source, reflected by or transmitted through the object to be measured, and transmitted through the filter by a first light receiving unit, and sending a first signal in response to the received first and the second lights through the first light receiving unit;
receiving by a second light receiving unit, light of a different path from the light received by the first light receiving unit, and sending a second signal in response to the received light through the second light receiving unit;
obtaining a difference signal between the first signal traveling through the first light receiving unit and the second signal traveling through the second light receiving unit by a difference extracting unit; and
generating information of the object to be measured based on the signal obtained from the difference extracting unit by an information generating unit.

15. The measuring method according to claim 14, further comprising:
stopping an output of light from the first light source that outputs the light to the object to be measured;
assigning firstly a predetermined first wavelength to a first filter which the light that is output from the first light source and transmitted through the object to be measured and the light that is output from the second light source and transmitted through the object to be measured can reach and which transmits the light of the assigned wavelength;
storing firstly a difference signal between the first signal output from the first light receiving unit that outputs the first signal according to the light transmitted through the first filter and the second signal output from the second light receiving unit that outputs the second signal according to the light transmitted through a second filter which scattered light that is output from the first light source and transmitted through the object to be measured and the light that is output from the second light source and transmitted through the object to be measured can reach and which transmits the light of a second wavelength that is output from the first light source;
outputting the light from the first light source;
storing secondly a difference signal between the signal output from the first light receiving unit and the signal output from the second light receiving unit as a step following the outputting step;
storing thirdly a difference signal between the signal stored in the first storing step and the signal stored in the second storing step;
assigning secondly the second wavelength to the first filter; and
correcting the difference signal between the first signal output from the first light receiving unit and the second signal output from the second light receiving unit with the signal that is stored in the third storing step as a step following the second assigning step;
wherein the information of the object to be measured is generated from the signal corrected in the correction step.

16. The measuring method according to claim 14, further comprising:
stopping an output of light from the first light source that outputs the light to the object to be measured;
assigning firstly a predetermined first wavelength to a first filter which the light that is output from the first light source and reflected by the object to be measured and the light that is output from the second light source and reflected by the object to be measured can reach and which transmits the light of the assigned wavelength;
storing firstly a difference signal between the first signal output from the first light receiving unit that outputs the first signal according to the light transmitted through the first filter and the second signal output from the second light receiving unit that outputs the second signal according to the light transmitted through the second filter which scattered light that is output from the first light source and reflected by the object to be measured and the light that is output from the second light source and reflected by the object to be measured can reach and which transmits the light of a second wavelength that is output from the first light source;
outputting the light from the first light source;
storing secondly a difference signal between the signal output from the first light receiving unit and the signal output from the second light receiving unit as a step following the outputting step;
storing thirdly a difference signal between the signal stored in the first storing step and the signal stored in the second storing step;
assigning secondly the second wavelength to the first filter; and
correcting the difference signal between the first signal output from the first light receiving unit and the second signal output from the second light receiving unit with the signal that is stored in the third storing step as a step following the second assigning step;
wherein the information of the object to be measured is generated from the signal corrected in the correction step.

17. The measuring method according to claim 14, further comprising:
stopping an output of light from the first light source that outputs the light to the object to be measured;
controlling firstly the first light receiving unit, which can receive measuring light that is output from the first light source, transmitted through the object to be measured, and then transmitted through the filter that transmits the light of the predetermined wavelength and the light that is output from the second light source, transmitted through the object to be measured, and then transmitted through the filter and which outputs a signal according to the received light, so that the first light receiving unit does not respond to the light;
storing firstly a difference signal between the signal output from the first light receiving unit and the signal output from the second light receiving unit, which can receive scattered light that is output from the first light source and transmitted through the object to be measured and the light that is output from the second light source and transmitted through the object to be measured and which outputs a signal according to the received light, as a step following the first control step;
outputting the light from the first light source;

storing secondly a difference signal between the signal from the first light receiving unit and the signal from the second light receiving unit as a step following the outputting step;

storing thirdly a difference signal between the signal stored in the first storing step and the signal stored in the second storing step;

controlling secondly the first light receiving unit so that the first light receiving unit responds to the light; and correcting the difference signal between the first signal from the first light receiving unit and the second signal from the second light receiving unit with the signal that is stored in the third storage step as a step following the second control step;

wherein the information of the object to be measured is generated from the signal corrected in the correction step.

18. The measuring method according to claim 14, further comprising:

stopping an output of light from the first light source that outputs the light to the object to be measured;

controlling firstly the first light receiving unit, which can receive measuring light that is output from the first light source, reflected by the object to be measured, and then transmitted through the filter that transmits the light of the predetermined wavelength and the light that is output from the second light source, reflected by the object to be measured, and then transmitted through the filter and which outputs a signal according to the received light, so that the first light receiving unit does not respond to the light;

storing firstly a difference signal between the signal output from the first light receiving unit and the signal output from the second light receiving unit, which can receive scattered light that is output from the first light source and reflected by the object to be measured and the light that is output from the second light source and reflected by the object to be measured and which outputs a signal according to the received light, as a step following the first control step;

outputting the light from the first light source;

storing secondly a difference signal between the signal from the first light receiving unit and the signal from the second light receiving unit as a step following the outputting step;

storing thirdly a difference signal between the signal stored in the first storing step and the signal stored in the second storing step;

controlling secondly the first light receiving unit so that the first light receiving unit responds to the light; and correcting the difference signal between the first signal from the first light receiving unit and the second signal from the second light receiving unit with the signal that is stored in the third storage step as a step following the second control step;

wherein the information of the object to be measured is generated from the signal corrected in the correction step.

\* \* \* \* \*